(12) United States Patent
Stefanov

(10) Patent No.: US 11,484,667 B2
(45) Date of Patent: Nov. 1, 2022

(54) MEDICAMENT DELIVERY DEVICE

(71) Applicant: SHL MEDICAL AG, Zug (CH)

(72) Inventor: Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 507 days.

(21) Appl. No.: 16/744,428

(22) Filed: Jan. 16, 2020

(65) Prior Publication Data

US 2020/0147324 A1   May 14, 2020

Related U.S. Application Data

(63) Continuation of application No. 15/737,896, filed as application No. PCT/EP2016/062023 on May 27, 2016, now Pat. No. 10,525,213.

(30) Foreign Application Priority Data

Jun. 19, 2015  (SE) .................................. 1550857-5

(51) Int. Cl.
*A61M 5/50* (2006.01)
*A61M 5/20* (2006.01)
(Continued)

(52) U.S. Cl.
CPC .......... *A61M 5/502* (2013.01); *A61M 5/2033* (2013.01); *A61M 5/3157* (2013.01);
(Continued)

(58) Field of Classification Search
CPC .......... A61M 5/20; A61M 5/50; A61M 5/502; A61M 5/2033; A61M 5/3205;
(Continued)

(56) References Cited

U.S. PATENT DOCUMENTS 5,478,316 A  12/1995  Bitdinger et al.
7,758,550 B2  7/2010  Bollenbach et al.
(Continued)

FOREIGN PATENT DOCUMENTS

JP  H07-222799 A  8/1995
JP  2008-212631 A  9/2008
(Continued)

OTHER PUBLICATIONS

Office Action issued in Japanese Patent Application No. 2017-565738 dated Dec. 18, 2018.

*Primary Examiner* — Tiffany Legette
(74) *Attorney, Agent, or Firm* — McDonnell Boehnen Hulbert & Berghoff LLP

(57) ABSTRACT

The present invention relates to a medicament delivery device comprising a housing, a biased medicament delivery member guard arranged movable in relation to the housing from a proximally extended position to a retracted position, a power pack comprising a plunger rod and a force element arranged to act on said plunger rod, which power pack is actuated by a release clip movable in relation to the housing and arranged to said plunger rod for releasably holding said plunger rod with the force element in a tensioned state; a rotator rotatably arranged inside said housing, which rotator is arranged with a guide element and a medicament delivery member guard lock element on its outer surface, wherein said medicament delivery member guard is arranged with release clip activation elements operably arranged to act on said release clip for releasing said plunger rod, and wherein said medicament delivery member guard is further arranged with a rotator activator element arranged to cooperate with said guide element for turning said rotator, upon movement of said medicament delivery member guard to the retracted position, and wherein, upon movement of said medicament delivery member guard back to the extended position, said (Continued)

rotator activator element will engage said medicament delivery member guard lock element and lock said medicament delivery member guard in a shielding position after removal of said medicament delivery device from a medicament delivery site.

19 Claims, 9 Drawing Sheets

(51) Int. Cl.
  *A61M 5/315* (2006.01)
  *A61M 5/32* (2006.01)
(52) U.S. Cl.
  CPC ... *A61M 5/3204* (2013.01); *A61M 2005/2013* (2013.01); *A61M 2005/2073* (2013.01); *A61M 2005/3208* (2013.01); *A61M 2005/3247* (2013.01); *A61M 2005/3267* (2013.01); *A61M 2005/5033* (2013.01); *A61M 2205/582* (2013.01); *A61M 2205/583* (2013.01); *A61M 2205/6063* (2013.01)
(58) Field of Classification Search
  CPC ...... A61M 5/31583; A61M 2005/2073; A61M 2005/3247; A61M 2005/3267; A61M 2005/5026; A61M 2005/5033; A61M 2205/273

See application file for complete search history.

(56) References Cited

U.S. PATENT DOCUMENTS

| | | |
|---|---|---|
| 8,062,255 B2 | 11/2011 | Brunnberg et al. |
| 8,460,245 B2 | 6/2013 | Guillermo et al. |
| 9,156,458 B2 | 11/2015 | Giambattista et al. |
| 2008/0147006 A1 | 6/2008 | Brunnberg et al. |
| 2008/0262438 A1 | 10/2008 | Bollenbach et al. |
| 2011/0034902 A1 | 2/2011 | Markussen |
| 2014/0350516 A1 | 11/2014 | Schwab et al. |

FOREIGN PATENT DOCUMENTS

| | | |
|---|---|---|
| JP | 2008-229344 A | 10/2008 |
| JP | 2010-533529 A | 10/2010 |
| JP | 2012-511350 A | 5/2012 |
| WO | 2009010591 A2 | 1/2009 |
| WO | 2009040602 A2 | 4/2009 |
| WO | 2010066592 A2 | 6/2010 |
| WO | 2011123024 A1 | 10/2011 |
| WO | 2014095424 A1 | 6/2014 |
| WO | 2015132234 A1 | 9/2015 |

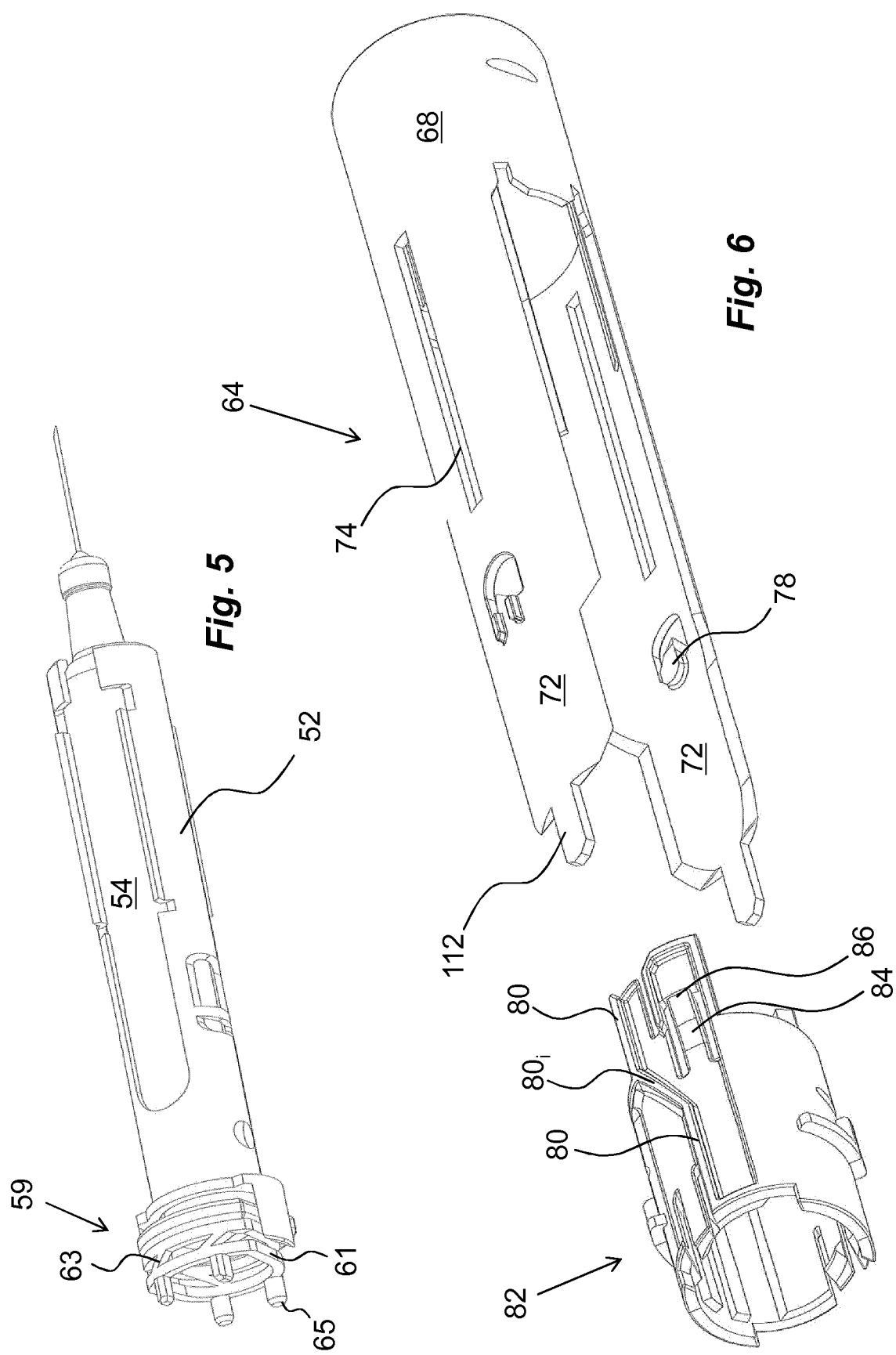

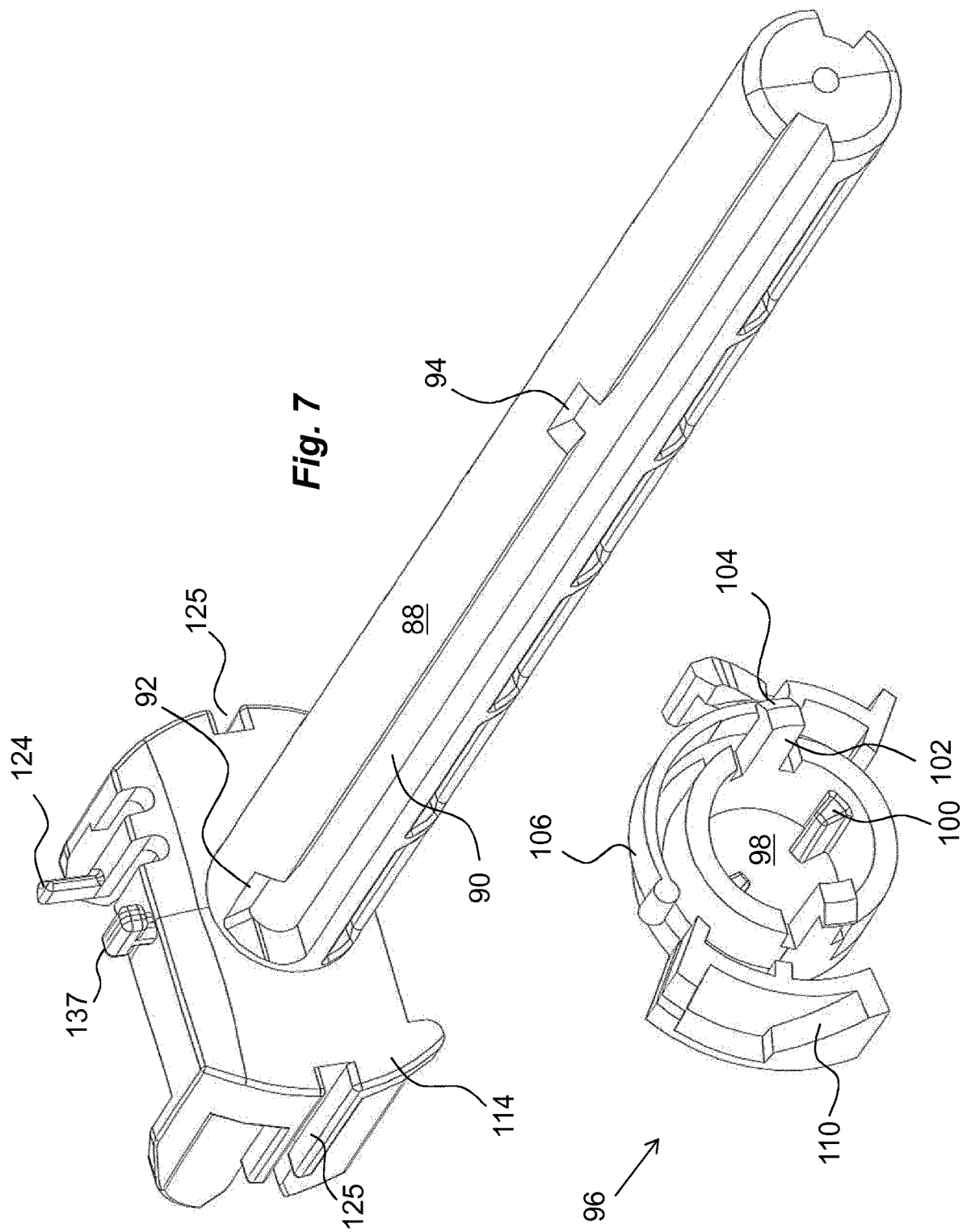

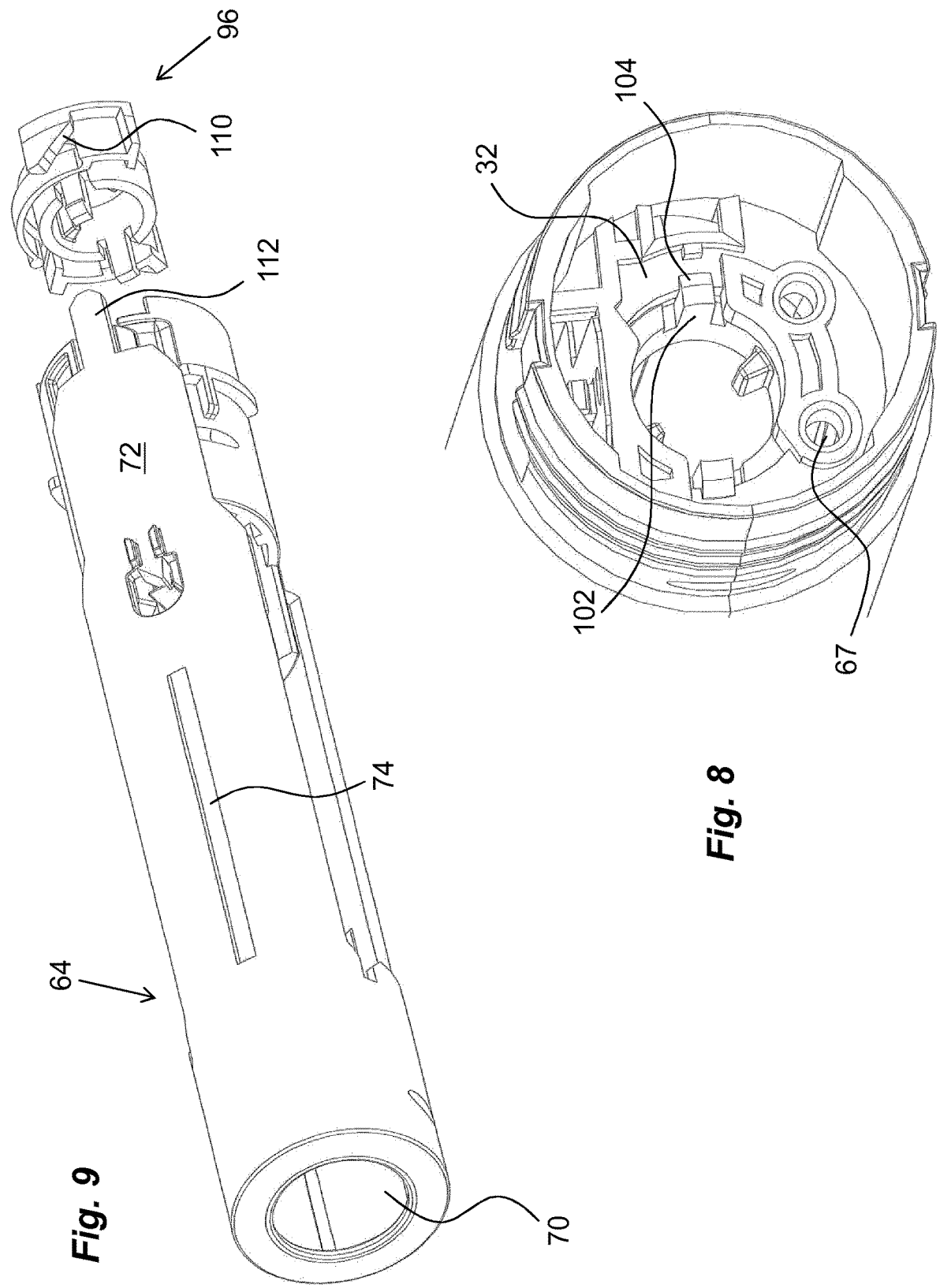

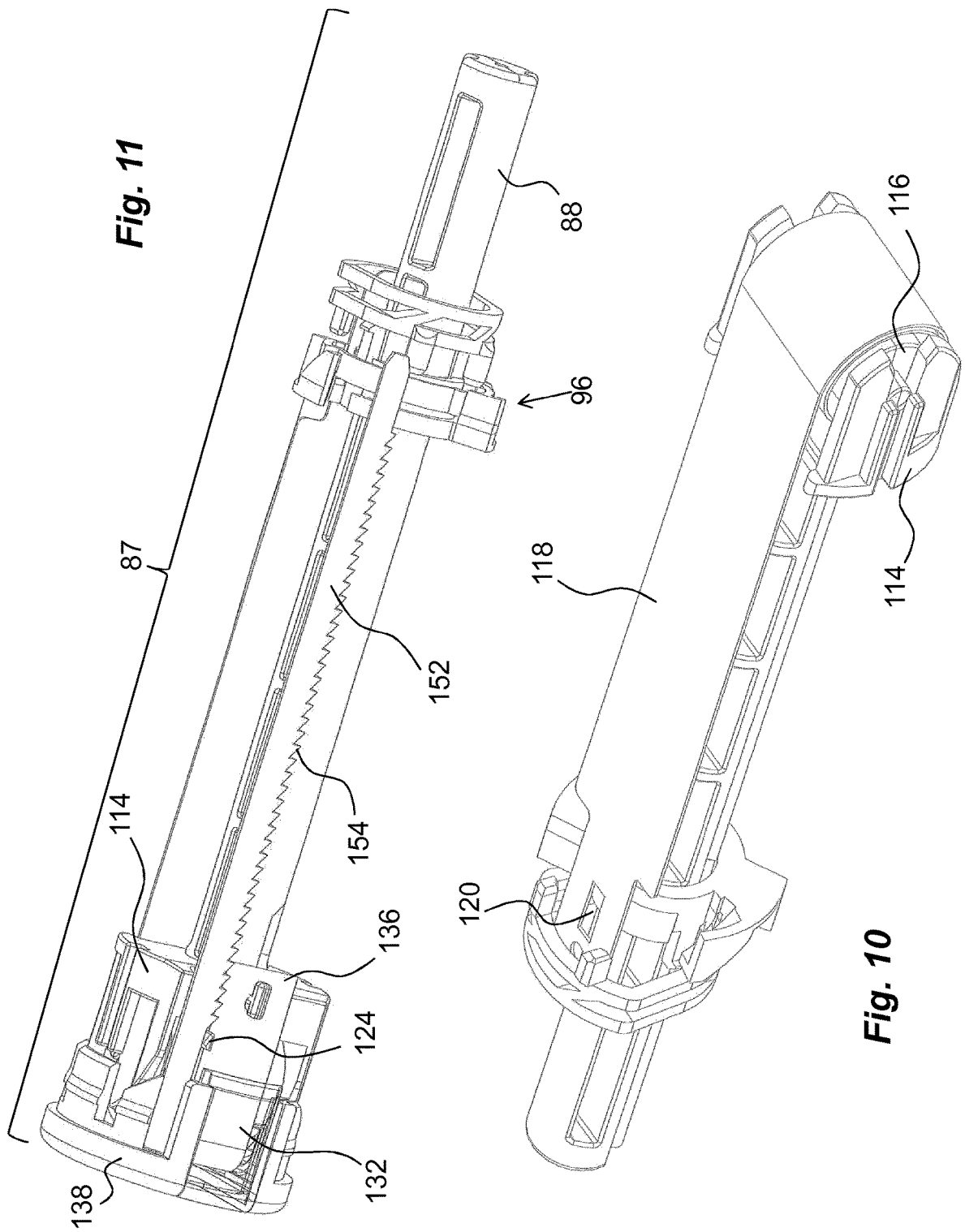

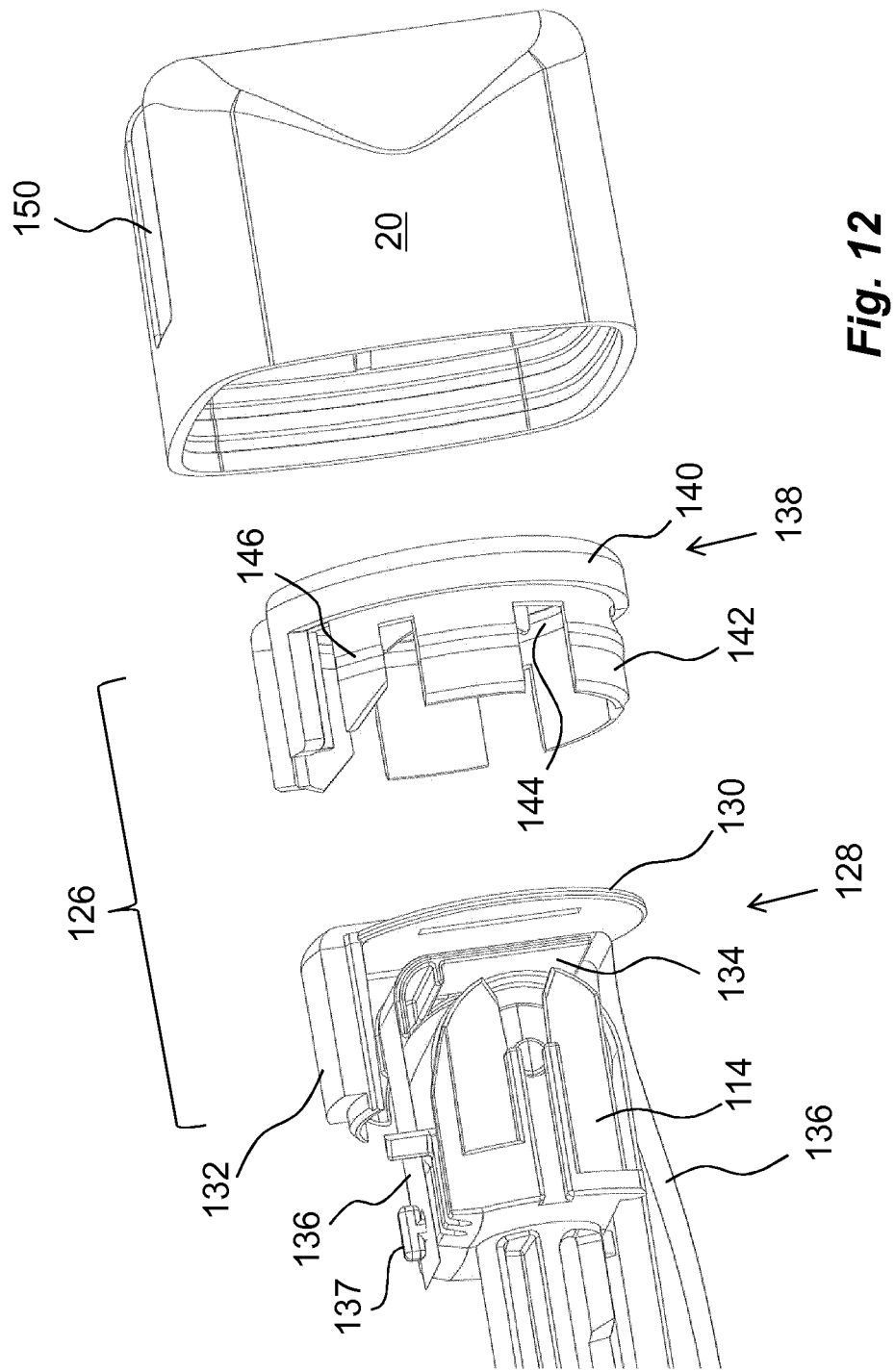

MEDICAMENT DELIVERY DEVICE

CROSS REFERENCE TO RELATED APPLICATIONS

The present application is a continuation of U.S. patent application Ser. No. 15/737,896, filed Dec. 19, 2017, now U.S. patent Ser. No. 10/525,213, issued Jan. 7, 2020, which is a U.S. National Phase Application pursuant to 35 U.S.C. § 371 of International Application No. PCT/EP2016/062023 filed May 27, 2016, which claims priority to Swedish Patent Application No. 1550857-5 filed Jun. 19, 2015. The entire disclosure contents of these applications are herewith incorporated by reference into the present application.

TECHNICAL AREA

The present invention relates to a medicament delivery device comprising a number of automatic features.

BACKGROUND

There are an increasing number of medicament delivery devices on the market that are arranged with a number of different automatic functions and features. In particular automatic injection is a feature that is often provided on injectors. An automatic injection facilitates the handling of a medicament delivery device as compared to manual injection, because an injection sequence, and in particular the start, requires quite high forces. This is because of a rather high break loose force for moving the stopper. A higher force requirement is also present if the medicament has a higher viscosity and/or a narrow injection needle.

Another feature that is important and that is often automatic is the shielding of an injection needle after the medicament delivery device has been withdrawn. This is often performed by a needle guard that extends in the proximal direction by a spring or the like when the medicament delivery device is removed from the dose delivery site and surrounds the needle. In the fully extended position, the needle guard is locked by appropriate locking elements so that the needle guard cannot be pushed back into the medicament delivery device again, exposing the injection needle.

The above mentioned functions may be triggered/activated by the movement of the needle guard both when retracting into the medicament delivery device as well as extending out of the medicament delivery device. One solution that utilises these features is disclosed in document WO2011/123024A1. The medicament delivery device disclosed therein is arranged with a rotator, which is provided with guide ridges on its outer surface. These guide ridges are arranged to cooperate with protrusions on distally extending arms of a longitudinally movable needle guard such that the rotator is turned when the needle guard is moved in the distal direction during a penetration sequence. The turning of the rotator will cause a release of a plunger rod that is in a tensioned state, whereby the release will cause a dose of medicament to be expelled through a medicament delivery member. The turning of the rotator will also cause a blocking element to be positioned in line with the protrusions as seen in a longitudinal direction such that when the needle guard extends after removal of the medicament delivery device, the protrusions will pass the blocking element and lock the needle guard in the extended shielding position.

Even though this solution has its advantages, for some types of medicament delivery devices, the releasing of the tensioned plunger rod requires a separate mechanism dedicated to the holding and releasing of the plunger rod for performing an injection sequence. In those cases, the start of the injection sequence and the locking of the needle guard would be performed by separate mechanisms.

SUMMARY

In the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, creme/gel dispensers, etc. The medicament delivery devices may be of either disposable type or re-usable type and may be provided with medicament containers suitably arranged for specific drugs in specific forms.

Further, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

The aim of the present invention is to provide a medicament delivery device that is arranged with separate mechanisms. This aim is obtained by a medicament delivery device provided with the features of the independent patent claim. Preferable solutions form the subject of the dependent patent claims.

According to a main feature, a medicament delivery device comprises a housing and a biased medicament delivery member guard arranged movable in relation to the housing from a proximally extended position to a retracted position. The medicament delivery device is further arranged with a power pack comprising a plunger rod and a force element arranged to act on the plunger rod.

According to the invention, the power pack may be actuated by a release clip arranged to the plunger rod for releasably holding the plunger rod with the force element in a tensioned state. The release clip is comprised in the mechanism for holding and releasing the tensioned plunger rod for performing an injection sequence of a dose of medicament. In this respect, the medicament delivery member guard may be arranged with release clip activation elements operably arranged to act on the release clip for, upon movement of the medicament delivery member guard, releasing the plunger rod.

As a separate functional feature, a rotator may be rotatably arranged inside the housing, where the rotator may be arranged with guide elements on its outer surface. In this respect, there may be rotator activator elements on the medicament delivery member guard arranged to cooperate with the guide elements for turning the rotator when the medicament delivery member guard is moved to the retracted position.

Further, a medicament delivery member guard lock element may be arranged on the rotator, wherein, upon movement of the medicament delivery member guard back to the extended position, the medicament delivery member guard lock element will engage and lock the medicament delivery member guard in a shielding position after removal of the medicament delivery device from a medicament delivery site. Thus, here the locking function is separate and arranged to the rotator. The rotator then has one function and that is to lock the medicament delivery member guard in the extended position after removal of the medicament delivery device after completed dose delivery.

According to one feasible solution, the release clip activation elements may comprise distally directed tongues arranged to act on activation surfaces on the release clip. Thus, when the medicament delivery member guard is moving in the distal direction in relation to the rest of the device, the distally directed tongues are moving to act on the release clip. In that respect, the activation surfaces may comprise inclined surfaces such that interaction between the tongues and the inclined surfaces causes a turning of the release clip from a blocking position to a release position.

These and other aspects of, and advantages with, the present invention will become apparent from the following detailed description of the invention and from the accompanying drawings.

BRIEF DESCRIPTION OF THE FIGURES

In the following detailed description of the invention, reference will be made to the accompanying drawings, of which

DETAILED DESCRIPTION

Figure 3:
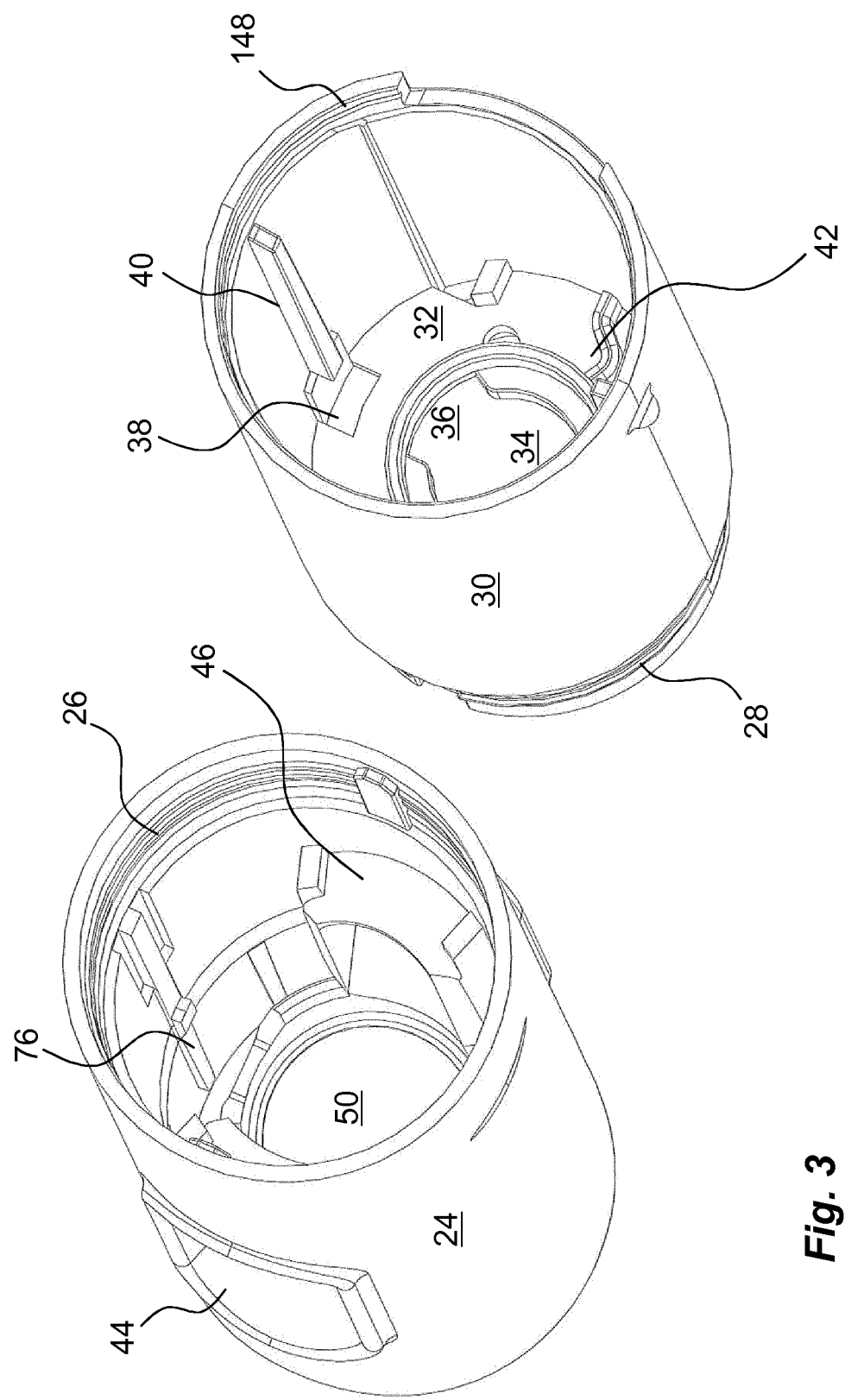

The medicament delivery device shown in the drawings comprises an outer housing 10 with a generally tubular shape and with a somewhat rectangular cross-section, having a distal end 12 and a proximal end 14. The distal end 12 of the housing 10 is arranged with a number of attachment elements 16 that are arranged to cooperate with corresponding attachment elements 18 on an end cap 20. The proximal end 14 of the outer housing 10 is arranged with a central opening 22 through which a proximal inner housing part 24 is extending. The proximal inner housing part 24 is arranged with attachment elements 26 FIG. 3, on an inner surface of its distal end, which attachment elements 26 are arranged to cooperate with corresponding attachment elements 28 on a distal inner housing part 30. The distal inner housing part 30 is arranged with a transversal wall 32 having a central passage 34. The central passage 34 is arranged with two oppositely positioned cut-outs 36. Further, two peripheral passages 38 are arranged in the wall 32 on opposite sides adjacent the inner walls of the distal inner housing part 30, FIGS. 3 and 4. A ridge 40, FIG. 3, is positioned in the longitudinal direction as seen from the peripheral passages 38, the function of which will be described below. Further a seat 42 is arranged on the distal surface of the transversal wall 32, FIG. 3, the function of which will be explained below.

Figure 4:
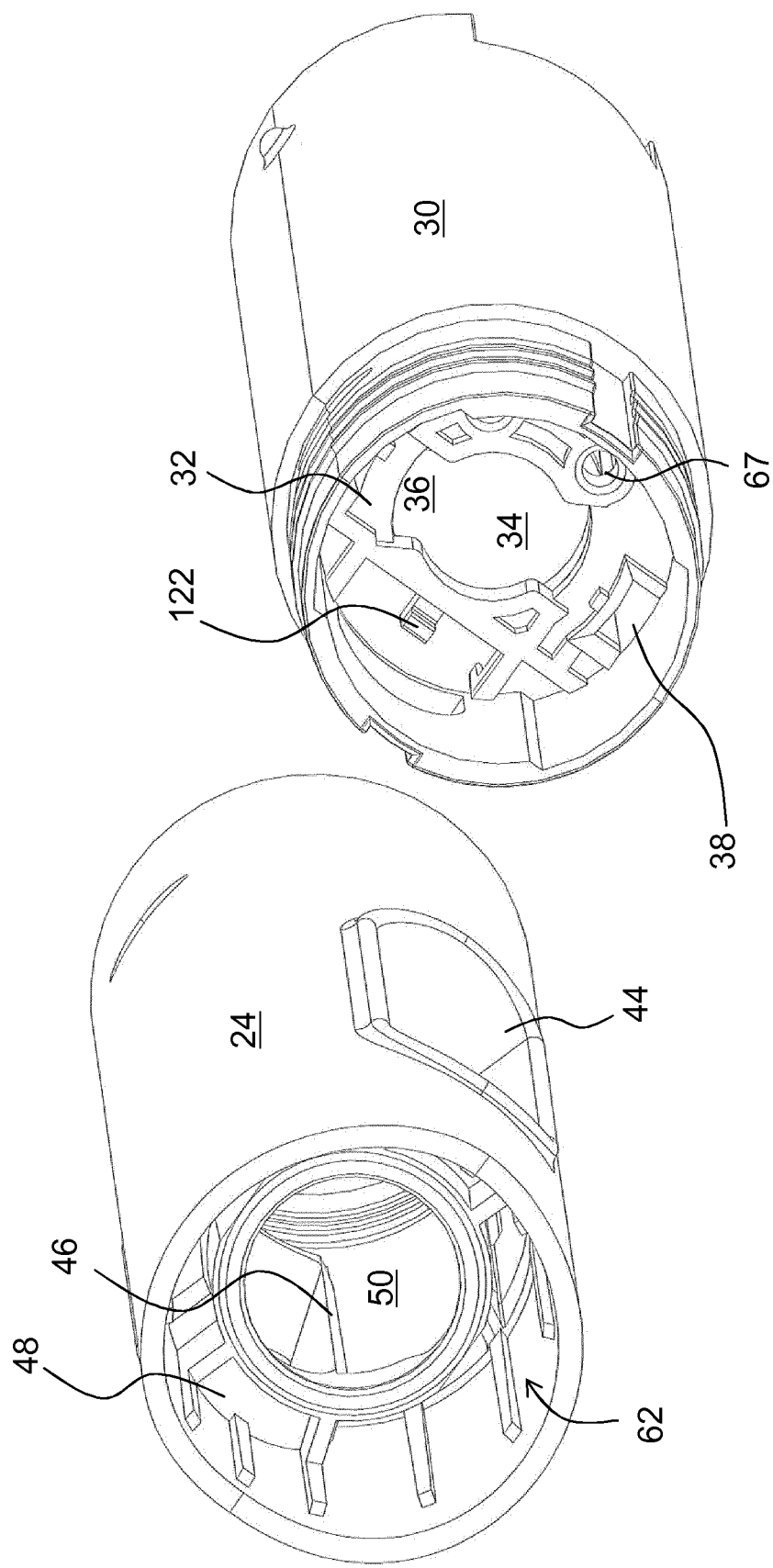

The proximal inner housing part 24 is further arranged with openings or windows 44. Each window is arranged with an inwardly directed circumferential ledge 46. As seen in FIG. 4, a support wall 48 is attached to the circumferential ledge 46, wherein the support wall 48 is arranged with a central passage 50. The edge of the central passage 50 as well as the inner edges of the circumferential ledges 46 of the windows 44 form support surfaces for a generally tubular medicament container holder 52, FIG. 1. The medicament container holder 52 is arranged to accommodate a generally tubular elongated medicament container 54 provided with a movable stopper 56 and arranged with a medicament delivery member 58 that in the embodiment shown is an injection needle, FIG. 2. It is however to be understood that other types of medicament delivery members such as nebulizers, mouth or nose pieces may be used, just to mention a few. The medicament delivery member 58 may be integrated with the medicament container 54 or may be an attachable part that may be connectable in many ways such as with threads, bayonet couplings, luer connections, and the like.

The medicament delivery member 58 is further surrounded by a removable medicament delivery member shield 60 that in the embodiment shown is in the form of a so called rigid needle shield 60. It is however to be understood that other types of medicament delivery member shields such as so called flexible needle shields may be used instead. Further, a medicament container damping element 59, FIGS. 2 and 5, is arranged between a distal end surface of the medicament container 54 and the proximally directed surface of the transversal wall 32. The damping element is made in a resilient material such as rubber or soft plastics. It comprises two ring-shaped members 61 interconnected by obliquely angled connection elements 63, providing a damping action. Distally directed protrusions 65 are intended to fit into corresponding holes 67 in the transversal wall 32, FIGS. 4 and 8.

Figure 1:
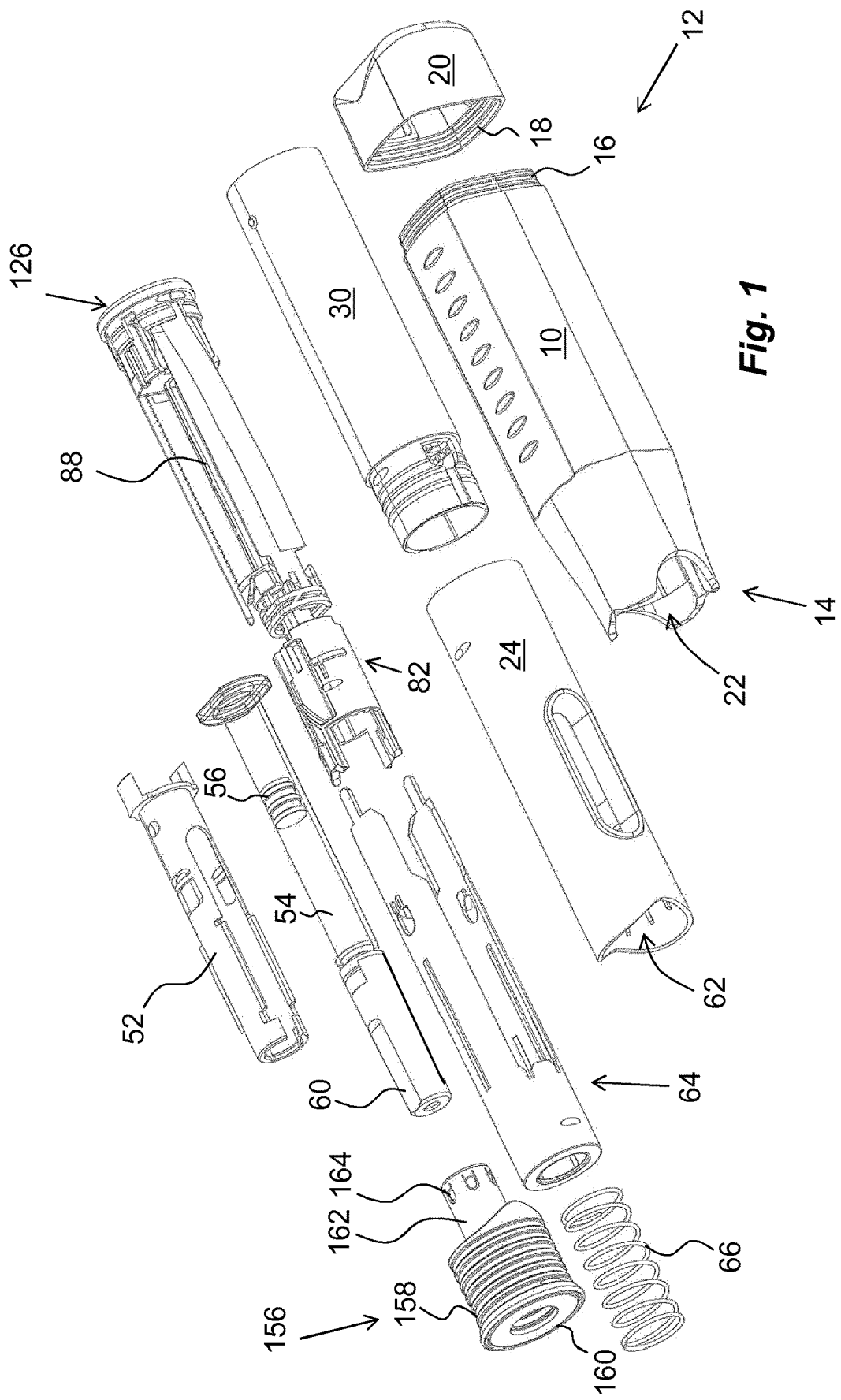
FIG. 1 shows an exploded view of one embodiment of a medicament delivery device, FIG. 2 show cross-sectional views of the medicament delivery device of FIG. 1, and FIGS. 3, 4, 5, 6, 7, 8, 9, 10, 11 and 12 show detailed views of components and sub-assemblies comprised in the medicament delivery device of FIG. 1.

The proximal inner housing part 24 is arranged with a central passage 62 through which a generally tubular medicament delivery member guard 64 protrudes, FIGS. 1 and 6. The medicament delivery member guard 64 is urged in the proximal direction by a medicament delivery member guard spring 66, which is arranged between a distally directed wall part of the medicament delivery member guard 64 and a proximally directed surface of the support wall 48 as seen in FIG. 2. The medicament delivery member guard 64 is provided with a proximal, generally tubular part 68 provided with a central passage 70, FIGS. 6 and 9. At the distal end of the tubular part 68, two arms 72 are extending in the distal direction. The arms 72 are arranged with longitudinally extending grooves 74, which are intended to cooperate with longitudinal guide ridges 76 on an inner surface of the proximal inner housing part 24. Further, the inner surfaces of the arms 72 are each arranged with rotator activator elements that in the embodiment shown are in the form a protrusion 78, FIG. 6. The protrusions 78 are arranged to cooperate with guide elements in the form of ridges 80 on an outer surface of a generally tubular rotator 82, FIG. 6. Some of the guide ridges 80, are extending inclined in relation to the longitudinal axis L of the medicament delivery device, the function of which will be described below. A proximal part of the rotator 82 is further arranged with proximally directed tongues 84, wherein the free ends of the tongues 84 are arranged with wedge-shaped outwardly directed protrusions 86, the function of which will be described below.

Figure 2A:
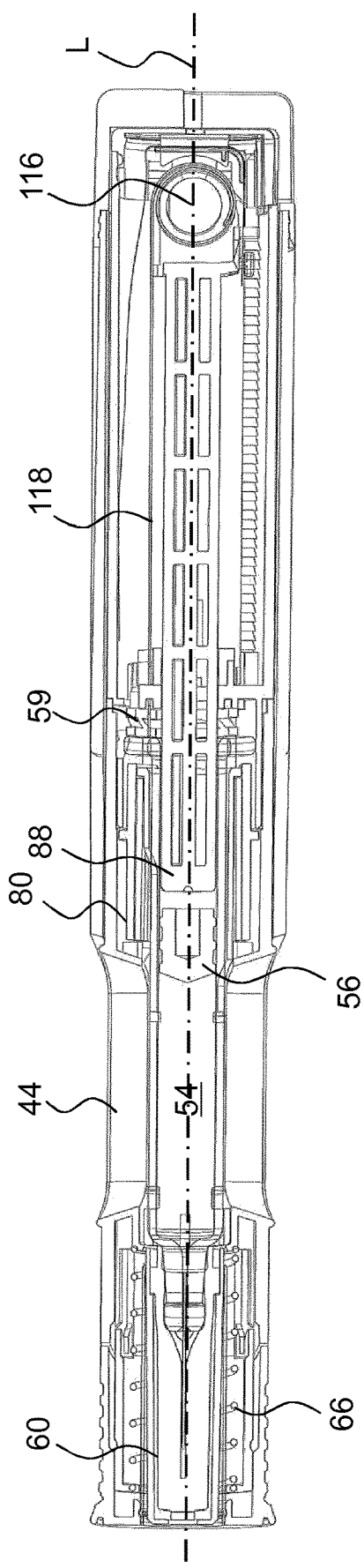
Figure 2B:
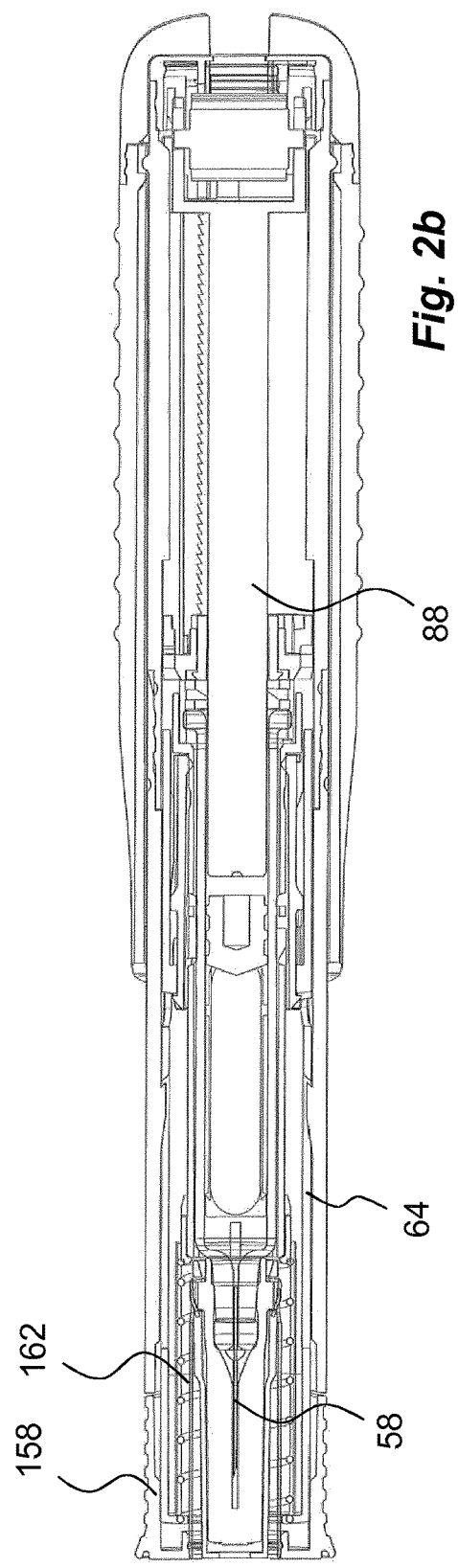

The medicament delivery device is further arranged with a power pack 87, FIG. 11, comprising an elongated plunger rod 88 that extends through the rotator 82, FIG. 2*a*. The plunger rod 88 is arranged with two longitudinal grooves 90 arranged on opposite sides, FIG. 7, which grooves 90 each are arranged with two cut-outs 92, 94, one cut-out 92 at a distal end of the plunger rod 88 and one cut-out 94 in the proximal area, FIG. 7. The plunger rod 88 is arranged to cooperate with a generally ring-shaped release clip element 96 having a central passage 98 through which the plunger rod 88 extends. The central passage 98 is arranged with inwardly extending ledges 100, which ledges 100 fit into the longitudinal grooves 90 of the plunger rod 88. They will also co-act with the cut-outs 92, 94 as will be explained. The release clip element 96 is further arranged to the proximal inner housing part 24 with a proximally directed surface in contact with the distally directed surface of the transversal wall 32 of the proximal inner housing part 24. The release clip element 96 is arranged with proximally extending arms 102 that are arranged to fit into the cut-outs 36 of the central passage 34 of the transversal wall 32, where the cut-outs 36 will limit the turning of the release clip element 96 as will be described. The free ends of the arms 102 are arranged with radially outwardly directed ledges 104, which ledges 104 are contacting the proximal surface of the transversal wall 32, thereby preventing movement of the release clip element 96 in the distal direction, FIG. 8.

The release clip element 96 is further arranged with a flexible arm 106, FIG. 7, that is curved and extending in the circumferential direction. The free end of the flexible arm 106 is seated in the seat 42 arranged on the transversal wall 32 of the proximal inner housing part 24. The release clip element 96 also comprises activation surfaces in the form of two proximally directed ridges 110 having a wedge-shaped form as seen in a longitudinal cross-section. The wedge-shaped ridges 110 are positioned generally adjacent the peripheral passages 38 of the transversal wall 32. The distal ends of the arms 72 of the medicament delivery member guard 64 are arranged with release clip activation elements that in the embodiment shown are arranged as distally directed tongues 112, FIG. 9, which tongues 112 are arranged to fit through the peripheral passages 38 of the transversal wall 32 of the inner distal housing part 30 and to contact the wedge-shaped ridges 110 of the release clip element 96, as will be described.

The power pack 87 is further arranged with a generally U-shaped bracket 114 arranged at the distal end of the plunger rod 88. The bracket 114 rotatably supports a roll 116, FIGS. 2a and 10. On the roll 116 a force element, e.g. a drive spring in the form of a coiled clock spring 118 is arranged having an inner end attached to the roll 116. The free end of the clock spring 118 is provided with a hole 120, FIG. 10, through which a fixed post 122 extends, FIG. 4, which post is integral with the transversal wall 32. The bracket 114 also comprises a transversally directed protrusion 124, FIGS. 7 and 11, having a wedge-shape as seen in a cross-section. The bracket 114 is supported in the transversal direction by the ridge 40 fitting into longitudinally extending grooves 125, FIG. 7, preventing any movement in that direction by the force of the spring 118.

An end lid 126 is attached to the distal end of the distal inner housing part, FIG. 12. The end lid 126 comprises an inner part 128, preferably in a transparent material. The inner part 128 has a disk-shaped body 130 and a proximally directed elongated magnifying glass part 132. The inner proximally directed surface of the body 130 is arranged with an L-shaped guide element 134. An information ribbon 136, provided with indicia on its outer surface, is attached to the U-shaped bracket 114 of the plunger rod 88 via a post 137, and runs around the L-shaped guide element 134, past the magnifying glass 132. The inner part 128 is attachable to a second outer part 138. The outer part 138 is arranged with a disk-shaped body 140 provided with proximally directed arms 142. On the inner surface of the arms 142, a circumferential groove 144 is arranged into which the body 130 of the inner part 128 fits. The outer surface of the arms 142 are arranged with circumferential protrusions 146, which are intended to fit into and interlock with corresponding circumferential grooves 148, FIG. 3, on the inner surface of a distal part of the distal inner housing part 30. The end cap 20 is arranged with a passage 150 in which the magnifying glass 132 fits when the medicament delivery device is assembled. An elongated proximally directed pin 152 is further attached to the second outer part 138, FIG. 11. The pin 152 is arranged with wedge-shaped teeth 154 along its length, which wedge-shaped teeth 154 are arranged to engage with the wedge-shaped protrusion 124 of the bracket 114, as will be described.

Finally the medicament delivery device comprises a medicament delivery member shield remover 156, FIG. 1. It comprises a generally tubular grip part 158 having an end wall 160. The distally directed surface of the end wall 160 is arranged with a seat in which a generally tubular grip element 162 is placed. The grip element 162 will be coaxial with and surrounding the medicament delivery member shield 60 when the medicament delivery member shield remover 156 is attached to the proximal end of the medicament delivery device. The grip element 162 comprises a number of generally proximally directed somewhat inwardly inclined tongues 164 that are engaging the outer surface of the medicament delivery member shield 60.

The device is intended to function as follows. When the medicament delivery device is delivered to a user, a medicament container 54 with an attached medicament delivery member shield 60 has been placed in the medicament container holder 52 and a medicament delivery member shield remover 156 has been attached to the proximal end of the medicament delivery device. The drive spring 118 of the power pack 87 has been coiled out and tensioned in that the plunger rod 88 has been pushed distally relative the release clip element 96 such that the inwardly directed ledges 100 in the central passage 98 of the release clip element 96 engage with the proximally positioned cut-outs 94 of the plunger rod 88, thereby holding the plunger rod 88 in a tensioned state. The release clip element 96 is urged and held in this position by the flexible arm 106 of the release clip element 96.

When now the medicament delivery device is to be used, the proximal end thereof is pressed against a dose delivery site. This causes the medicament delivery member guard 64 to move distally relative to the rest of the medicament delivery device. The protrusions on the inner surface of the arms 72 of the medicament delivery member guard 64 will come in contact with the inclined guide ridges 80 of the rotator 82, thereby turning the rotator 82. Further the distal ends of the tongues 112 of the medicament delivery member guard 64 will engage with and press on the inclined surfaces of the wedge-shaped ridges 110 of the release clip element 96. This action will cause the release clip element 96 to turn against the force of the flexible arm 106, until the proximally directed arms 102 hit side surfaces of the cut-outs 36 of the central passage 34. The turning of the release clip element 96 will cause the ledges 100 of the release clip element 96 to move out of the cut-outs 94 of the plunger rod 88.

The plunger rod 88 is now free to move and will be forced in the proximal direction by the force of the drive spring 118. The proximal end of the plunger rod 88 will act on the stopper 56, moving it in the proximal direction, thereby expelling a dose of medicament through the medicament delivery member 58. Since the plunger rod 88 is moving in the proximal direction, so is the bracket 114 and the wedge-shaped protrusion 124, such that it will move along and in contact with the teeth 154 of the elongated pin 152, causing audible and tactile information that a dose delivery sequence is performed. Further, the movement of the plunger rod 88 with the bracket 114 will pull the information ribbon 136 so that it moves past the magnifying glass 132 such that the indicia is visible through the magnifying glass 132, where the pattern of the indicia gives a visual indication that the dose delivery sequence is performed. The injection sequence is ended when the ledges 100 hit the distal end of the longitudinal groove 90, whereby the release clip 96 will be turned by the flexible arm 106 such that the ledges 100 fit into the distal cut-outs 92.

When now the dose has been delivered the medicament delivery device is removed from the site. This in turn will cause the medicament delivery member guard 64 to be moved in the proximal direction by the medicament delivery member shield spring 66 extending through the proximal end of the medicament delivery device and covering the medicament delivery member. Since the rotator 82 has been rotated, the protrusions 78 of the medicament delivery member guard 64 will slide over the wedge-shaped protrusions 86 of the rotator 82 and be placed proximally thereof, thereby locking the medicament delivery member guard 64 in the extended, covering position. The device can now be discarded in a safe manner.

It is to be understood that the embodiment described above and shown in the drawings is to be regarded only as a non-limiting example of the invention and that it may be modified in many ways within the scope of the patent claims.

The invention claimed is:

1. A medicament delivery device comprising:
   a housing;
   a biased medicament delivery member guard arranged movable in relation to said housing from a proximally extended position to a retracted position;
   a power pack comprising a plunger rod and a constant force spring arranged to act on said plunger rod;
   a release clip movable in relation to said housing and arranged to said plunger rod for releasably holding said plunger rod with the spring in a tensioned state;
   a rotator rotatably arranged inside said housing, wherein said rotator is arranged with a guide element and a medicament delivery member guard lock element; and
   a damping element arranged adjacent to a proximally directed surface of a transversal wall of the housing,
   wherein said medicament delivery member guard comprises a release clip activation element operably arranged to act on said release clip for releasing said plunger rod,
   wherein said medicament delivery member guard is further arranged with an actuator arranged to cooperate with said guide element for turning said rotator, upon movement of said medicament delivery member guard to the retracted position, and
   wherein, upon movement of said medicament delivery member guard back to the proximally extended position, said actuator engages said medicament delivery member guard lock element and locks said medicament delivery member guard in a shielding position after removal of said medicament delivery device from a medicament delivery site.

2. The medicament delivery device of claim 1, wherein the damping element is arranged such that, when a medicament container is placed in the medicament delivery device, the damping element is arranged between the proximally directed surface of the transversal wall of the housing and a distal end surface of the medicament container.

3. The medicament delivery device of claim 1, wherein said damping element is a separate component from said housing.

4. The medicament delivery device of claim 1, wherein said damping element is integral with said transversal wall.

5. The medicament delivery device of claim 1, wherein said damping element comprises resilient material comprising rubber or plastic.

6. The medicament delivery device of claim 1, wherein said damping element comprises two ring-shaped members interconnected by obliquely angled connectors.

7. The medicament delivery device of claim 1, wherein said rotator is arranged with said guide element and said medicament delivery member guard lock element on an outer surface of said rotator.

8. The medicament delivery device of claim 1, wherein the release clip actuates the power pack.

9. The medicament delivery device of claim 1, wherein the release clip activation element comprises a plurality of distally directed tongues.

10. The medicament delivery device of claim 9, wherein said plurality of distally directed tongues are arranged to act on at least one activation surface on said release clip.

11. The medicament delivery device of claim 10, wherein said release clip is arranged turnable inside said housing.

12. The medicament delivery device of claim 11, wherein said at least one activation surface comprises an inclined surface such that interaction between said plurality of distally directed tongues and said inclined surface causes a turning of said release clip from a blocking position to a release position.

13. The medicament delivery device of claim 1, wherein said spring comprises a drive spring.

14. The medicament delivery device of claim 1, further comprising:
   a roll rotatably attached to a distal end of said plunger rod, wherein said constant force spring is wound on said roll.

15. The medicament delivery device of claim 1, wherein said medicament delivery member guard is urged in a proximal direction by a medicament delivery guard spring.

16. The medicament delivery device of claim 15, wherein said medicament delivery guard spring is arranged between a distally directed wall part of said medicament delivery guard and a proximally directed surface of said housing.

17. The medicament delivery device of claim 1, further comprising:
   an indication protrusion configured to provide one or more of a tactile indication or an audible indication during a dose delivery sequence.

18. The medicament delivery device of claim 17, wherein said indication protrusion is capable of providing tactile indications during said dose delivery sequence.

19. The medicament delivery device of claim 17,
   wherein said indication protrusion comprises an elongated fixed pin arranged with teeth operably engaging a protrusion arranged to said plunger rod.

\* \* \* \* \*